United States Patent
Rowe

(10) Patent No.: US 10,245,363 B1
(45) Date of Patent: Apr. 2, 2019

(54) CATHETER-BASED PUMP FOR IMPROVING ORGAN FUNCTION

(71) Applicant: Stanton J. Rowe, Newport Coast, CA (US)

(72) Inventor: Stanton J. Rowe, Newport Coast, CA (US)

(73) Assignee: Stanton J. Rowe, Newport Coast, CA (US)

( * ) Notice: Subject to any disclaimer, the term of this patent is extended or adjusted under 35 U.S.C. 154(b) by 0 days.

(21) Appl. No.: 14/741,808

(22) Filed: Jun. 17, 2015

Related U.S. Application Data

(60) Provisional application No. 62/013,474, filed on Jun. 17, 2014.

(51) Int. Cl.
*A61M 1/12* (2006.01)
*A61M 1/10* (2006.01)
*A61M 25/10* (2013.01)

(52) U.S. Cl.
CPC .......... *A61M 1/125* (2014.02); *A61M 1/1029* (2014.02); *A61M 1/1072* (2013.01); *A61M 1/1086* (2013.01); *A61M 1/122* (2014.02); *A61M 25/1011* (2013.01); *A61M 2205/3344* (2013.01)

(58) Field of Classification Search
CPC .... A61M 1/10; A61M 1/1086; A61M 1/1072; A61M 2001/122
USPC ................. 604/101.04; 600/16–18
See application file for complete search history.

(56) References Cited

U.S. PATENT DOCUMENTS

| | | | | |
|---|---|---|---|---|
| 5,478,309 | A * | 12/1995 | Sweezer | A61M 1/10 604/101.04 |
| 5,765,568 | A * | 6/1998 | Sweezer, Jr. | A61M 1/10 128/898 |
| 6,136,025 | A * | 10/2000 | Barbut | A61F 2/90 604/530 |
| 6,544,216 | B1 * | 4/2003 | Sammler | A61M 25/0125 604/95.03 |
| 6,935,344 | B1 * | 8/2005 | Aboul-Hosn | A61M 1/3653 128/898 |
| 7,766,961 | B2 | 8/2010 | Patel et al. | |
| 2004/0163655 | A1 | 8/2004 | Gelfand et al. | |
| 2004/0210236 | A1 | 10/2004 | Allers et al. | |
| 2009/0112049 | A1 * | 4/2009 | Ahmed | A61M 1/1037 600/16 |
| 2011/0190874 | A1 | 8/2011 | Celermajer et al. | |
| 2012/0232457 | A1 | 9/2012 | Kandarpa | |

* cited by examiner

*Primary Examiner* — Christopher D Koharski
*Assistant Examiner* — Roland Dinga
(74) *Attorney, Agent, or Firm* — Nixon & Vanderhye P.C.

(57) ABSTRACT

Apparatus, systems, and methods in which a catheter-based pump is used are disclosed. The catheter-based pump is placed within the inferior vena cava of a patient. The catheter-based pump has a variable obstructor, such as a balloon or some other artificial obstruction, which is sized and dimensioned to compartmentalize the inferior vena cava into an upstream region and a downstream region of the inferior vena cava. The catheter-based pump is configured to pump blood from the upstream region to a fluid line that discharges blood to a discharge location in the downstream region. Thus, a suitable pressure gradient across the organ is provided, which can benefit organ function.

10 Claims, 4 Drawing Sheets

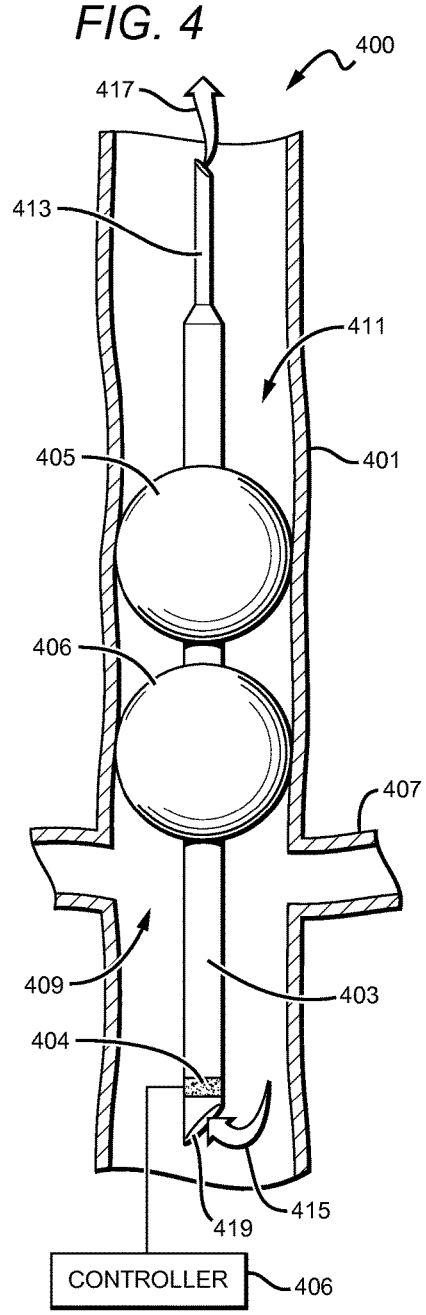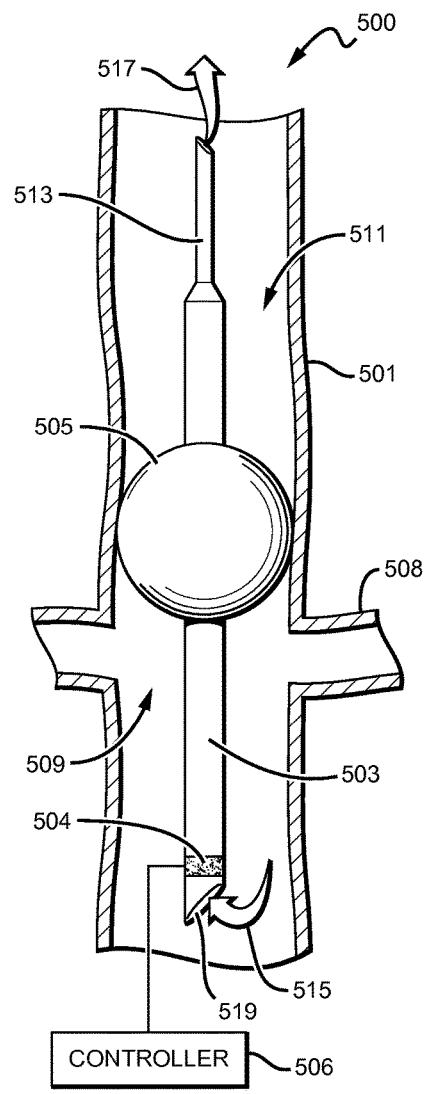

CATHETER-BASED PUMP FOR IMPROVING ORGAN FUNCTION

RELATED APPLICATION

This application claims priority to U.S. Provisional Application Ser. No. 62/013,474, filed Jun. 17, 2014, the entirety of which is incorporated by reference in its entirety.

FIELD OF INVENTION

The field of the invention is improving organ (e.g., kidney, liver) function by compartmentalizing the inferior vena cava in a patient.

BACKGROUND

The background description includes information that may be useful in understanding the present invention. It is not an admission that any of the information provided herein is prior art or relevant to the presently claimed invention, or that any publication specifically or implicitly referenced is prior art.

Acute heart failure occurs frequently in chronic heart failure, especially in Class III and IV patients, and is extraordinarily prevalent. It is characterized by peripheral edema, lung congestion, and often both. Patients are admitted to the hospital, and typically spend five inpatient days "drying out", through extended diuresis and inotropic support. Without hospitalization, patients risk death from acute heart failure and concomitant respiratory failure creating hypoxia due to pulmonary edema.

Decompensation from heart failure can eventuate into cardiohepatic syndrome, which is characterized by failure of the heart and liver, and cardiorenal syndrome, which is characterized by simultaneous heart and kidney failure. The primarily failing organ may be the heart or kidney, and it is often this failing organ that precipitates failure of the other. Treating acute cardiac decompensation is through potent diuresis by continuous or bolus loop diuretic infusion, vasodilators, and inotropic support. Potent diuretics stimulate the kidneys to excrete fluid to eliminate excess intravascular and extravascular fluid, but often eventuate in renal failure.

Some have contemplated catheter systems to increase renal perfusion and function. For example, Patel (U.S. Pat. No. 7,766,961) discloses a drain catheter for reducing the venous pressure of the renal system. The catheter is positioned in the renal vein, and an expandable member is inflated within the renal vein to occlude the renal vein from the venous system. An external reversible roller pump is used to extract blood from a distal tip of the catheter into a drain line. The extracted blood is then inserted back into the venous system through a return line in the femoral vein. While the drain catheter of Patel increases renal perfusion, the discharge of extracted blood in the femoral vein may cause unfavorable pressure changes in the venous system upstream of the renal veins.

Others have contemplated systems for controlling pressure in the venous system. Some examples of these systems include Kieval (U.S. Pat. Pub. 2013/0199806), Kandarpa (U.S. Pat. Pub. 2012/0232457), Gelfand (U.S. Pat. Pub. 2004/0163655), Allers (U.S. Pat. Pub. 2004/0210236) and Celermajer (U.S. Pat. Pub. 2011/0190874). However, such systems are typically overly complicated.

Others have contemplated blood pumps that can be positioned within a patient. For example, Rau (Canadian Pat. 2,250,993) discloses a blood pump that is connected to a catheter. The blood pump has a blocking device that separates a suction side from the delivery side. However, the blood pump is designed to be positioned at a site upstream of an organ within a blood vessel, such as an artery.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Thus, there is still a need for a device to mechanically improve the arterial-venous pressure gradient across an organ to thereby improve global organ function.

SUMMARY OF INVENTION

The present invention provides apparatus, systems, and methods in which organ function is improved using a catheter-based pump. In one aspect of the inventive subject matter, a catheter-based pump is placed within the inferior vena cava of a patient. The catheter-based pump has a variable obstructor, such as a balloon or other artificial obstruction, which is sized and dimensioned to compartmentalize the inferior vena cava into an upstream region and a downstream region. As used herein, a "variable obstructor" means an artificial obstruction that is configured to expand or inflate to obstruct fluid flow. The catheter-based pump is configured to pump blood from the upstream region to a fluid line that discharges blood to a discharge location in the downstream region.

The variable obstructor comprises a balloon, and more typically, an inflatable balloon. In some embodiments, the variable obstructor (e.g., a balloon or other artificial obstruction) has a diameter between 12 and 30 mm, inclusive, when fully inflated. It should be appreciated that the variable obstructor can completely occlude (i.e., prevent blood from flowing from the upstream region to the downstream region via the exterior of the catheter-based pump) and partially occlude (i.e., allow some blood to flow from the upstream region to the downstream region via the exterior of catheter-based pump) the inferior vena cava. As used herein, the terms "completely occlude" or "complete occlusion" means complete obstruction of flow. Additionally, it is contemplated that a second variable obstructor (e.g., a balloon or other artificial obstruction) can be positioned upstream of the renal vein ostium.

The catheter-based pump can draw blood from various locations and discharge blood at various locations. For example, the catheter-based pump can be dimensioned to draw blood upstream or downstream of the renal vein ostium. Similarly, the catheter-based pump can be dimensioned to discharge blood within 10 cm or within the right atrium of the patient's heart.

A pressure monitor is included in some embodiments to measure blood pressure within the upstream region of the inferior vena cava. The pressure monitor can be positioned within 2 cm of an intake valve of the catheter-based pump. Furthermore, a controller can co-operate with the pressure monitor to operate the catheter-based pump to maintain a suitable pressure in the upstream region of the inferior vena cava. An exemplary suitable pressure is a pressure between 5 and 15 mmHg, inclusive.

In another aspect, a method for improving renal function of a patient comprises steps of occluding an inferior vena cava downstream of a renal vein ostium to form an upstream region and a downstream region, and pumping blood from the upstream region to a discharge location in the downstream region during a time that the inferior vena cava is occluded.

The inferior vena cava can be partially occluded or completely occluded to improve renal function. The step of occluding can further include inserting a catheter-based pump through a femoral, jugular or subclavian vein of the patient. Additionally, or alternatively, a balloon is inflated to occlude the inferior vena cava or some other artificial obstruction occludes the inferior vena cava. It should be appreciated that occluding downstream of a hepatic vein ostium can encourage suitable perfusion of at least one of the kidney and the liver to improve kidney and liver function.

Blood is pumped from the upstream region to the downstream region of the inferior vena cava. Exemplary discharge locations of the blood in the downstream region include a distance within 10 cm of the right atrium of the patient's heart or within the right atrium of the heart. Thus, it is contemplated that the discharge line can be positioned to deliver blood in several discharge locations. The step of pumping blood can further include implanting a pump within the body of the patient.

In some embodiments, an operating procedure is completed which leaves the inferior vena cava occluded between the upstream and downstream regions, and a pump operates to move the blood from the upstream region to the discharge location. In other embodiments, an operating procedure is completed which leaves the inferior vena cava occluded between the upstream and downstream regions, and implants a pump that operates to move the blood from the upstream region to the discharge location.

In another aspect, a method of improving organ function of a patient comprises the steps of generating an at least partial occlusion in an inferior vena cava downstream of a renal vein ostium to form an upstream region and a downstream region, pumping blood from the upstream region to a discharge location in the downstream region during a time that the inferior vena cava is occluded, and adjusting the occlusion of the inferior vena cava based on a pressure of the upstream region to maintain a pre-determined pressure of the inferior vena cava.

In yet another aspect, a system comprising a catheter-based pump, a pressure monitor, and a controller is disclosed. The catheter-based pump has a variable obstructor configured for placement within an inferior vena cava to compartmentalize the inferior vena cava into an upstream region and downstream region. The pressure monitor is configured to measure blood pressure within the upstream region and generates a pressure signal. The controller is operationally coupled to the catheter-based pump and the pressure monitor, and controls a diameter of the variable obstructor based on the pressure signal. It should be appreciated that the catheter-based pump is configured to pump blood from the upstream region to a fluid line configured to discharge the blood to a discharge location in the downstream region.

One should appreciate that the disclosed subject matter provides many advantageous technical effects including mechanically improving arterial-venous pressure gradient across the kidney (renal artery-renal vein/IVC) to thereby improve global kidney function. For example, this device can be used to improve renal perfusion in patients having acutely decompensated heart failures, which typically causes pressure gradient problems in the kidney of a patient. Thus, pharmacological procedures to reduce the risk of kidney failure in acutely decompensated heart failure patients are reduced by using this device for improving renal perfusion and function. While the catheter-based pump can be used to enhance renal perfusion to improve kidney function, it should be appreciated the catheter-based pump can also be used to improve liver function to thereby reduce the risk of liver congestion or other liver problems.

Various objects, features, aspects and advantages of the inventive subject matter will become more apparent from the following detailed description of preferred embodiments, along with the accompanying drawing figures in which like numerals represent like components.

SUMMARY OF DRAWINGS

FIG. 4 is a perspective view of an embodiment of a catheter-based pump having a second variable obstructor.

FIG. 5 is a perspective view of an embodiment of a catheter-based pump positioned downstream of a hepatic vein ostium.

DETAILED DESCRIPTION

The following discussion provides example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

A system for improving organ (e.g., kidney, liver, etc.) function in a patient using a catheter-based pump is disclosed. The catheter-based pump includes a variable obstructor (e.g., balloon or artificial obstruction) that is sized and dimensioned to compartmentalize the inferior vena cava into an upstream region and a downstream region. The variable obstructor can be inserted within a patient in a deflated or flattened orientation and can be inflated or expanded to compartmentalize the inferior vena cava. The variable obstructor is typically positioned downstream of a renal vein ostium. The catheter-based pump is configured to pump blood from the upstream region to a fluid line configured to discharge the blood to a discharge location in the downstream region. Thus, the arterial-venous pressure gradient across an organ is improved in a patient, and acutely decompensated heart failure patients or other patients suffering from pressure gradient problems across organs, such as the kidney, can be treated to improve perfusion.

Figure 1:
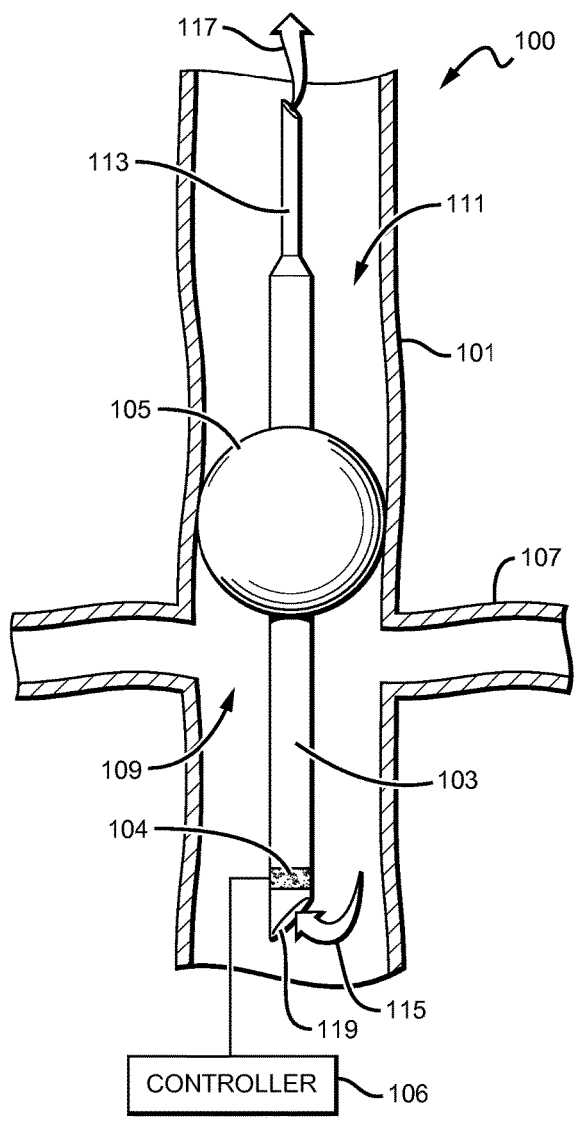
FIG. 1 is a perspective view of an embodiment of a catheter-based pump positioned downstream of a renal vein ostium.

FIG. 1 shows an embodiment of a system 100 for improving renal function in a patient having an inferior vena cava 101. System 100 includes a catheter-based pump 103 having a variable obstructor 105 that is positioned downstream of a renal vein ostium 107. Variable obstructor 105 is sized and dimensioned to compartmentalize inferior vena cava 101 into an upstream region 109 and a downstream region 111 of inferior vena cava 101. Catheter-based pump 103 is used to pump blood from upstream region 109 to a fluid line 113 that discharges the blood to a discharge location 117 in the downstream region 111.

Catheter-based pump 103 can be inserted into inferior vena cava 101 through various means. For examples, catheter-based pump 103 can be inserted through at least one of the jugular, subclavian, or femoral veins. Fluoroscopy or ultrasound can be used to position catheter-based pump 103. Furthermore, it is contemplated that a heparin coating can be applied to the catheter-based pump 103.

Catheter-based pump 103 has variable obstructor 105 that can be inflated to occlude inferior vena cava 101. It should be appreciated that variable obstructor 105 is typically deflated when catheter-based pump 103 is being positioned in inferior vena cava 101. Once catheter-based pump 103 is in a suitable position, variable obstructor 105 is inflated to occlude inferior vena cava 101. Complete occlusion and partial occlusions of inferior vena cava 101 using variable obstructor 105 are contemplated to improve renal function. FIG. 1 shows variable obstructor 105 fully inflated to provide complete occlusion of inferior vena cava 101, such blood flow from upstream region 109 to downstream region 111 can only be achieved through catheter-based pump 103 in this embodiment. In other words, blood does not flow between the outside surface of variable obstructor 105 and the inside wall of the inferior vena cava 101. It is contemplated that variable obstructor 105 can have a diameter between 12 and 30 mm, inclusive, when fully inflated.

In some embodiments, an outer surface of variable obstructor 105 is in contact with the inside wall of inferior vena cava 101 for complete occlusion as shown in FIG. 1. In other words, variable obstructor 105, when inflated, can have a diameter equal to or greater than the diameter of inferior vena cava 101. In other embodiments, it is contemplated that variable obstructor 105 can partially occlude inferior vena cava 101. Partial occlusion includes at least 50% obstruction of flow, more typically at least 75% obstruction of flow, and most typically at least 85% obstruction of flow. In such embodiments, variable obstructor 105 can be sized and dimensioned to fully inflate to partially occlude inferior vena cava 101 or variable obstructor 105 can be sized and dimensioned to partially inflate in order to partially occlude inferior vena cava 101. Suitable methods of inflating variable obstructor 105 include, but are not limited to, external pumping devices and pumping devices within the patient (e.g., an implanted screw pump).

As shown in FIG. 1, catheter-based pump 103 is positioned downstream of renal vein ostium 107. In this embodiment, catheter-based pump 103 is dimensioned to draw blood upstream of renal vein ostium 107. However, it is contemplated that catheter-based pump 103 can be dimensioned to draw blood downstream of renal vein ostium 107. FIG. 1 shows that blood can be drawn through an intake valve 119 where it travels through the catheter-based pump 103 into a fluid line 113 and the blood is discharged at a discharge location 117 to bypass variable obstructor 105. It is contemplated that intake valve 119 is positioned within 10 cm, and more preferably within 5 cm, of renal vein ostium 107. Additionally, or alternatively, intake valve 119 can be positioned in renal vein ostium 107. A flow path 115 shows an exemplary flow path of blood into intake valve 119 of catheter-based pump 103.

Catheter-based pump 103 can also be positioned to discharge the blood at various locations downstream of renal vein ostium 107. For example, it is contemplated that fluid line 113 can be positioned to discharge the blood within 10 cm of the right atrium of the patient's heart. In another example, fluid line 113 can be positioned to discharge blood within the right atrium of the patient's heart. While FIG. 1 does not expressly show the distance between the discharge point of fluid line 113 and the patient's heart, FIG. 1 should be interpreted generically as representing embodiments having sizes and dimensions as stated herein, including for example, as having a fluid line sized and dimensioned to discharge blood within 10 cm of the right atrium of the patient's heart or within the right atrium of the patient's heart.

To ensure adequate pressure for renal function, a pressure monitor 104 can be implemented. Pressure monitor 104 can be configured to measure blood pressure within the upstream region 109 of inferior vena cava 101. Additionally, or alternatively, pressure monitor 104 can be configured to measure blood pressure within downstream region 111 of inferior vena cava 101. It is contemplated that pressure monitor 104 can integrated into catheter-based pump 103 and positioned within 2 cm of intake valve 119 of catheter-based pump 103. However, it should be appreciated that pressure monitor 104 can be separate from catheter-based pump 103. For example, pressure monitor 104 can be a separate component that is coupled to catheter-based pump 103 and positioned within at least one of inferior vena cava 101 and renal vein ostium 107 to measure pressure at certain locations within the patient.

A controller can be used in conjunction with pressure monitor 104 to control various aspects of system 100. For example, the controller can co-operate with pressure monitor 104 to operate catheter-based pump 103 to maintain pressure in inferior vena cava 101 between 5 and 15 mmHg. In another example, the controller can co-operate with the mechanism that inflates variable obstructor 105 to maintain pressure in inferior vena cava 101 between 5 and 15 mmHg. It is contemplated that the controller is a real-time controller, and that controller can be accessed electronically (e.g., RFID, WiFi, Bluetooth®, cellular network, etc). System 100 can be a closed-loop system, such that catheter-based pump 103 is operated to maintain suitable pressures in inferior vena cava 101 and/or renal vein 107 by the controller, which receives real-time signals from pressure monitor 104. Controller can also generate alerts when the pressure in inferior vena cava 101 is above 15 mmHG and below 5 mmHG, and also generate an alert if catheter-based pump 103 is improperly positioned within inferior vena cava 101.

Catheter-based pump 103 can be an impeller pump (e.g., Impella® pump) configured to pump blood from upstream region 109 to downstream region 111 through catheter-based pump 103 and into fluid line 113 as shown in FIG. 1. It is contemplated that catheter-based pump 103 can be implanted within the patient. Additionally, or alternatively, catheter-based pump 103 can include an extracorporeal pump (e.g., a reversible roller pump). Moreover, it is contemplated that a blood filtration device can be coupled to the external pump to filter blood when needed before delivery into the downstream region of the inferior vena cava. However, it should be appreciated that an external pump is not needed to pump blood from upstream region 109 to downstream region 111. Thus, blood that is pumped from upstream region 109 to downstream region 111 can remain within the patient, and more typically, within inferior vena cava 101. As a result, the need to draw blood outside of the patient to an extracorporeal pump (e.g., reversible roller pump) is eliminated.

Figure 2:
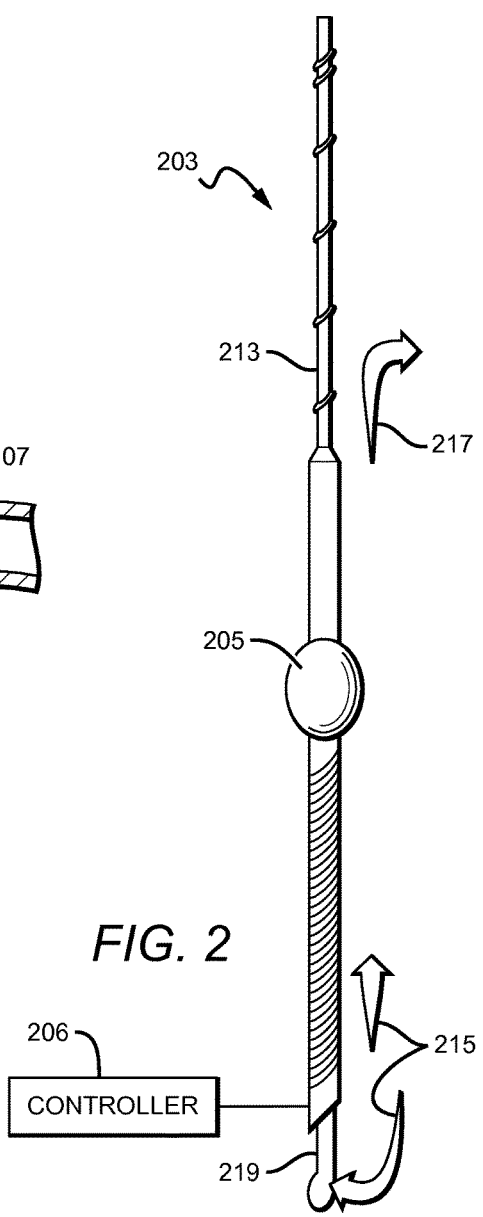
FIG. 2 is a perspective view of an embodiment of a catheter-based pump.

FIG. 2 shows an embodiment of a catheter-based pump 203. Similar to the catheter-based pump described above, catheter-based pump 203 has a variable obstructor 205, an intake valve 219, and a fluid line 213. It should be noted that similarly named components can be configured to operate as described in the various embodiments (e.g., it is contemplated that variable obstructor 205 can be configured to comprise the same features described above with respect to variable obstructor 105). Blood flows through a path 215 within catheter-based pump 203 to a discharge location 217. It is contemplated that discharge location 217 can be located at any position along fluid line 213. As described above, catheter-based pump 203 is an impeller pump that is configured to pump blood. However, catheter-based pump 203 can also include other types of pumps that are suitable to pump blood from an upstream region of an inferior vena cava to a downstream region of the inferior vena cava. It is contemplated that catheter-based pump is housed in the end or near the end of a guiding catheter used to place catheter-based pump in a suitable location.

Figure 3:
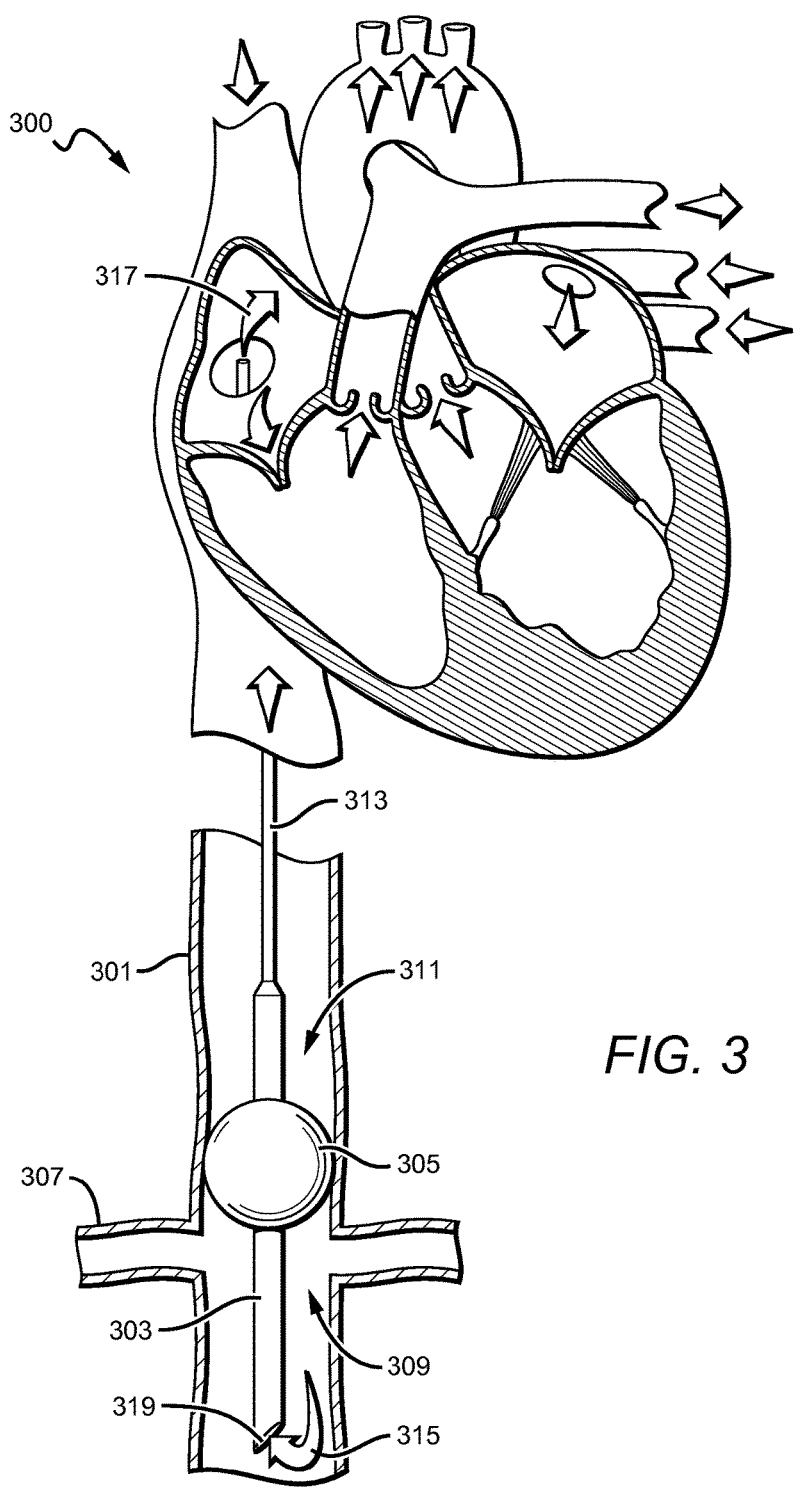
FIG. 3 is a perspective view of an embodiment of a catheter-based pump that is configured to discharge blood within the right atrium of a heart.

FIG. 3 show a system 300 of an embodiment of a catheter-based pump 303 that is positioned to discharge blood within the right atrium of the heart. Catheter-based pump 303 has a variable obstructor 305 that is fully inflated at a position downstream of a renal vein ostium 307. Blood is drawn using an intake valve 319 to bypass variable obstructor 305 through catheter-based pump 303 into a fluid line 313, which discharges blood at a discharge location 317 inside the right atrium of the heart. An exemplary flow path of blood drawn into intake valve 319 is shown in flow path 315. Thus, renal perfusion is improved in the patient.

Although only a single variable obstructor has been shown in the embodiments described thus far, it should be noted that the catheter-based pump can include a second variable obstructor as shown in FIG. 4. System 400 has a catheter-based pump 403 having a variable obstructor 405 and a second variable obstructor 406 that are positioned downstream of a renal vein ostium 407. While FIG. 4 shows variable obstructor 405 and second variable obstructor 406 fully inflated to completely occlude inferior vena cava 401, it is contemplated that only one of variable obstructor 405 and second variable obstructor 406 completely occlude inferior vena cava 401 or that both variable obstructor 405 and second variable obstructor 406 partially occlude inferior vena cava 401. Additionally, or alternatively, second variable obstructor can be positioned upstream or downstream of renal vein ostium 407. In other words, only a single variable obstructor is slightly superior to renal vein ostium 107.

It should be appreciated that second variable obstructor 406 can be placed upstream (i.e., inferior or below) of renal vein ostium 107 if a patient experiences little peripheral edema. Such positioning of the second variable obstructor 406 allows the catheter-based pump 403 to operate more effectively in lowering renal vein pressures. In such a case, second variable obstructor 406 can be half the diameter of inferior vena cava 401.

In another aspect, the inventor discovered a method for improving renal function of a patient. The method includes steps of occluding an inferior vena cava downstream of a renal vein ostium to form an upstream region and a downstream region, and pumping blood from the upstream region to a discharge location in the downstream region during a time that the inferior vena cava is occluded. While the embodiments thus far have disclosed occluding downstream of the renal vein ostium, it is contemplated that renal function can also be improved by occluding downstream of a hepatic vein ostium.

In contemplated embodiments, the step of occluding can further comprise inserting a catheter-based pump through a vein of the patient. For example, the catheter-based pump can be inserted through the jugular, femoral or the subclavian vein to position the catheter-based pump in the inferior vena cava. Catheter-based pump can be positioned in the inferior vena cava using fluoroscopy or ultrasound. It is contemplated that the catheter-based pump can be implanted within the body of the patient.

Blood can be pumped to various points in the downstream region using a fluid line to deliver the pumped blood. For example, contemplated methods include a step of positioning the fluid line to deliver the pumped blood within 15 cm of the right atrium of the patient's heart, and more preferably within 10 cm of the right atrium of the patient's heart. In another example, contemplated methods include a step of positioning a fluid line within the right atrium of the heart to deliver the pumped blood.

The pressure of the venous system is an important factor for renal function. As such, contemplated methods include a step of automatically maintaining pressure within upstream region of the inferior vena cava between 5 and 15 mmHg, inclusive. The pressure can be maintained using a pressure monitor and controller to co-operate with the pump. The controller can be a real-time controller that reacts to pressure changes in the upstream region of the inferior vena cava so that a safe pressure (e.g., 5 and 15 mmHg) is maintained.

Contemplated methods further include completing an operating procedure which leaves the inferior vena cava occluded between the upstream and downstream regions, and a pump operates to move the blood from the upstream region to the discharge location. In another embodiment, an operating procedure is completed which leaves the inferior vena cava occluded between the upstream and downstream regions, and implants a pump that operates to move the blood from the upstream region to the discharge location.

While some of the embodiments described are related to improving renal function, it should be appreciated that liver function can also be improved. FIG. 5 shows a system 500 having a catheter-based pump 503 positioned downstream of a hepatic vein ostium 508. Catheter-based pump 503 has a variable obstructor 505 that is fully inflated to completely occlude inferior vena cava 501 and form an upstream region 509 and a downstream region 511. However, it is contemplated that variable obstructor 505 can be configured to partially occlude inferior vena cava 501. Furthermore, catheter-based pump 503 can include a second variable obstructor that is positioned upstream or downstream of hepatic vein ostium 508.

Blood is drawn from a position upstream of hepatic vein ostium 508 through intake valve 519 and into catheter-based pump 503 to bypass variable obstructor 505 in FIG. 5. It is contemplated that catheter-based pump can also draw blood from a position downstream of hepatic vein ostium 508. Blood travels through catheter-based pump 503 into fluid line 513 and is discharged at a discharge location 517. Similar to that described above, fluid line 513 can be positioned to provide a discharge location 517 within 10 cm of the right atrium of the patient's heart or within the right atrium of the patient's heart. Thus, catheter-based pump 503 improves perfusion and function of the liver. It should be noted that renal function is also improved by positioning catheter-based pump 503 downstream of hepatic vein ostium 508 to occlude inferior vena cava 501.

Figure 6:
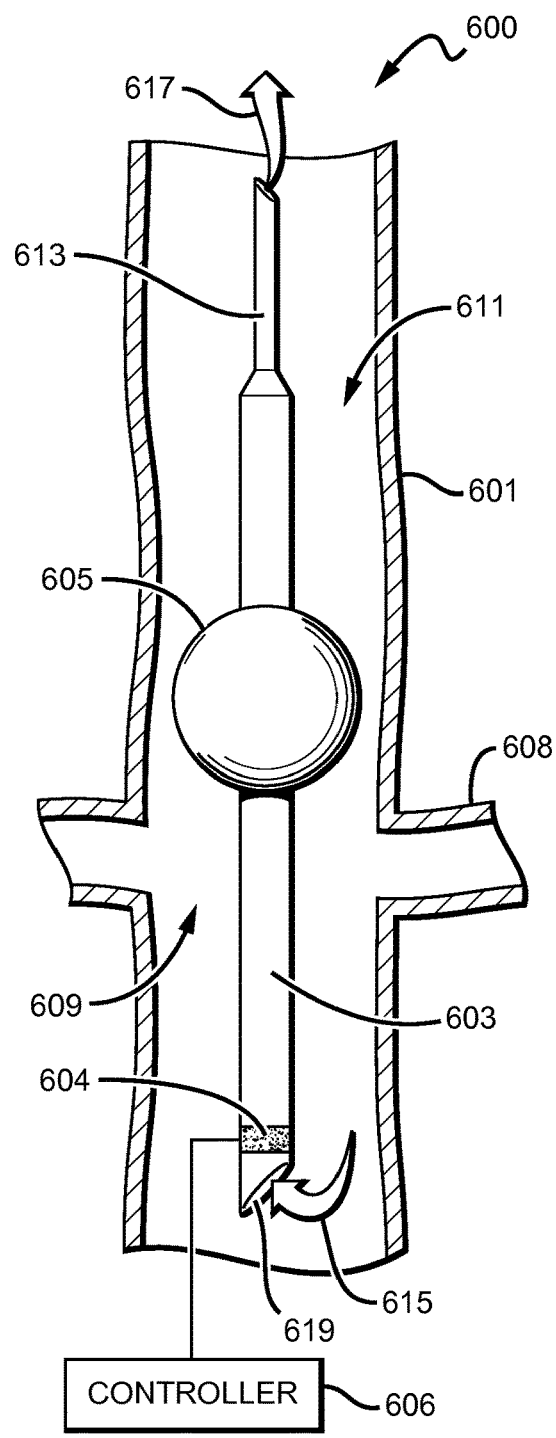
FIG. 6 is a perspective view of an embodiment of a catheter-based pump that is inflated to partially occlude the inferior vena cava.

In another aspect, a system 600 is disclosed having a catheter-based pump 603 with a variable obstructor 605 as shown in FIG. 6. Variable obstructor 605 is configured for placement within an inferior vena cava 601 at a position downstream of a renal vein ostium 608, and is further configured to inflate and partially occlude inferior vena cava 601 between an upstream region 609 and a downstream region 611. Catheter-based pump 603 is configured to pump blood from upstream region 609 to a fluid line 613 that is fluidly coupled to catheter-based pump 603 and configured to discharge the blood to a discharge location 617 in downstream region 611. However, unlike a complete occlusion, some blood flows around the perimeter of variable obstructor 605 from upstream region 609 to downstream region 611. It should be appreciated that variable obstructor 605 can be a balloon or other artificial obstruction.

Catheter-based pump 603 can include a pressure monitor 604 that is configured to measure the pressure in upstream region of inferior vena cava 609. As shown in FIG. 6, pressure monitor 604 can be located near intake valve 619. Furthermore, a controller 606 can be coupled to pressure monitor 604 and catheter-based pump 603 to control a pump rate of catheter-based pump 603 and/or a diameter of variable obstructor 605 to maintain a pre-determined pressure in upstream region 609.

In yet another aspect, a method for improving organ function is contemplated. The method comprises steps of generating an at least partial occlusion in an inferior vena cava downstream of a renal vein ostium to form an upstream region and a downstream region, pumping blood from the upstream region to a discharge location in the downstream region during a time that the inferior vena cava is occluded, and adjusting the occlusion of the inferior vena cava based on a pressure of the upstream region to maintain a pre-determined pressure of the inferior vena cava.

It is contemplated that the fluid line can be positioned to deliver pumped blood within 10 cm of the right atrium of the patient's heart. Additionally, or alternatively, the fluid line can be positioned to deliver pumped blood within the right atrium of the patient's heart.

Similar to the embodiments described above, the catheter-based pump can be inserted through a femoral, jugular or subclavian vein of the patient. Moreover, the step of generating the at least partial occlusion comprises inflating a balloon to occlude the inferior vena cava. It is also contemplated that the step of generating the at least partial occlusion generates the at least partial occlusion downstream of a hepatic vein ostium.

In yet another aspect, a system is disclosed comprising a catheter-based pump having a variable obstructor (e.g., balloon or other artificial obstruction) configured for placement within an inferior vena cava to compartmentalize the inferior vena cava into an upstream region and downstream region. The system further includes a pressure monitor that is configured to (i) measure blood pressure within the upstream region and (ii) generate a pressure signal. A controller is operationally coupled to the catheter-based pump and the pressure monitor, and is configured to control a diameter of the variable obstructor based on the pressure signal. It should be appreciated that controlling the diameter of the variable obstructor allows for an increase and a decrease in the degree of occlusion of the inferior vena cava. Thus, it is contemplated that the controller is configured to increase the diameter of the variable obstructor to completely occlude the inferior vena cava and to decrease the diameter of the variable obstructor to partially occlude the inferior vena cava to maintain a pre-determined pressure in at least one of an upstream region and a downstream region in the inferior vena cava.

The catheter-based pump is configured to pump blood from the upstream region to a fluid line configured to discharge the blood to a discharge location in the downstream region, wherein the fluid line is fluidly coupled to the catheter-based pump. It is contemplated that the catheter-based pump is positioned downstream of a renal vein ostium, and even downstream of a hepatic vein ostium.

The fluid line can be configured to discharge the blood within 10 cm of the right atrium of the patient's heart. Additionally, or alternatively, the fluid line can be configured to discharge the blood within the right atrium of the patient's heart.

The pressure monitor can have many suitable locations. For example, the pressure monitor can be positioned within 2 cm of an intake valve of the catheter-based pump. In another example, the pressure monitor can be positioned within 2 cm of the discharge location.

The controller is configured to operate the catheter-based pump to maintain a pre-determined pressure in at least one of the upstream region and downstream region of the inferior vena cava. While the controller can adjust the diameter of the variable obstructor, it is contemplated that the controller is further configured to control a pump rate of the catheter-based pump. The controller can be configured to control the pump rate to maintain the pressure signal between 5 and 15 mmHg in the upstream region of the inferior vena cava. Additionally, or alternatively, the controller can be configured to control the diameter of the variable obstructor to maintain a pressure signal between 5 and 15 mmHg in the upstream region of the inferior vena cava. As discussed above, it is contemplated that the variable obstructor comprises an inflatable balloon or an artificial obstruction.

In another aspect, a kit is disclosed comprising a delivery catheter and a catheter-based pump and a fluid line as described in any of the embodiments above, wherein the delivery catheter and the catheter-based pump and the fluid line are sterile and packaged.

While the systems and methods described above disclose a variable obstructor used to occlude an inferior vena cava, it is contemplated that many suitable devices can be used to occlude the inferior vena cava, such as a balloon. Other suitable devices to occlude the inferior vena cava include a temporary covered expandable stent or a valve or some other structural obstruction can be used to occlude the inferior vena cava and form an upstream region and a downstream region.

The systems and methods disclosed herein can be used to complement and reduce the polypharmacy used to treat acutely decompensated heart failure patients. Decompensated heart failure patients typically have compromised arterial-venous pressure gradient across the kidneys (renal artery-renal vein/IVC) due to chronically elevated right sided pressures. However, this pressure gradient is mechanically improved using the systems and methods herein to thereby improve global kidney function.

In addition, it should be appreciated that the systems and methods disclosed herein may effectively enhance natural diuresis, protect renal function, lower detrimental vasoactive renal catecholamines, and possibly protect against renal failure, renal injury and cardiorenal syndrome. By improving global kidney function, the pharmacologic burden in chronic heart failure patients is lessened by shorter hospitalization of the patient.

As used in the description herein and throughout the claims that follow, the meaning of "a," "an," and "the" includes plural reference unless the context clearly dictates otherwise. Also, as used in the description herein, the meaning of "in" includes "in" and "on" and the meaning of "or" includes either or both, unless the context for in and or clearly dictates another meaning.

Also, as used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Moreover, and unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A method for improving renal function of a patient, comprising:
   mechanically occluding an inferior vena cava downstream of a renal vein ostium to form an upstream region and a downstream region of the inferior vena cava; and
   mechanically pumping blood through the inferior vena cava from the upstream region to a discharge location in the downstream region while the inferior vena cava is occluded, wherein the blood remains in the inferior vena cava while being mechanically pumped.

2. The method of claim 1, wherein the step of mechanically occluding further comprises inserting a catheter-based pump through a femoral, jugular or subclavian vein of the patient.

3. The method of claim 1, wherein the step of mechanically pumping blood further comprising implanting a catheter-based pump within the body of the patient.

4. The method of claim 1, further comprising positioning a fluid line to deliver the pumped blood within 10 cm of the right atrium of the patient's heart.

5. The method of claim 1, further comprising positioning a fluid line to deliver the pumped blood within the right atrium of the patient's heart.

6. The method of claim 1, further comprising automatically maintaining pressure within upstream region of the inferior vena cava between 5 and 15 mmHg, inclusive.

7. The method of claim 1, further comprising completing an operating procedure which leaves the inferior vena cava occluded between the upstream and downstream regions, and a pump operates to move the blood from the upstream region to the discharge location.

8. The method of claim 1, further comprising completing an operating procedure which leaves the inferior vena cava occluded between the upstream and downstream regions, and implants a pump that operates to move the blood from the upstream region to the discharge location.

9. The method of claim 1, wherein the step of occluding comprises occluding the inferior vena cava downstream of a hepatic vein ostium.

10. The method of claim 1, wherein the step of occluding further comprises inflating a variable obstructor to occlude the inferior vena cava.

* * * * *